(12) United States Patent
Hauser

(10) Patent No.: US 9,956,063 B2
(45) Date of Patent: May 1, 2018

(54) ELECTRIC MOTORIZED TOOTHBRUSH WITH ROTATING SPINDLES

(71) Applicant: David Hauser, Merrick, NY (US)

(72) Inventor: David Hauser, Merrick, NY (US)

( * ) Notice: Subject to any disclaimer, the term of this patent is extended or adjusted under 35 U.S.C. 154(b) by 52 days.

(21) Appl. No.: 15/215,250

(22) Filed: Jul. 20, 2016

(65) Prior Publication Data

US 2018/0021118 A1    Jan. 25, 2018

(51) Int. Cl.
*A46B 13/02*    (2006.01)
*A61C 17/34*    (2006.01)
*A46B 9/04*    (2006.01)
*A46B 9/02*    (2006.01)

(52) U.S. Cl.
CPC .......... *A61C 17/3472* (2013.01); *A46B 9/026* (2013.01); *A46B 9/04* (2013.01); *A46B 13/02* (2013.01); *A61C 17/349* (2013.01); *A61C 17/3418* (2013.01); *A61C 17/3445* (2013.01)

(58) Field of Classification Search
CPC .... A61C 17/349; A61C 17/3418; A46B 13/02
See application file for complete search history.

(56) References Cited

U.S. PATENT DOCUMENTS

| | | | | |
|---|---|---|---|---|
| 2,628,377 A | * | 2/1953 | Cockriel | A61C 17/228 15/167.1 |
| 3,925,841 A | * | 12/1975 | Caliendo | A61C 17/26 15/23 |
| 5,428,855 A | * | 7/1995 | Li | A61C 17/26 15/23 |

* cited by examiner

*Primary Examiner* — Randall Chin
(74) *Attorney, Agent, or Firm* — Robert J. Hess; Hess Patent Law Firm

(57) ABSTRACT

An electric motorized toothbrush with a pair of bristle units spaced apart from each other by a gap and a third bristle unit bordering the gap by being closer to each of the bristle units of the pair than the bristle units of the pair are to each other. A motorized gear transmission, via associated spindles, rotates the pair of bristle units in opposite directions and either rotates or reciprocates the third bristle unit. The bristle units of the pair include a respective cylinder and bristles that extend radially outward from the respective cylinder and the bristles may be of varying lengths. The bristles rotate in a direction away from the gum line while the teeth are inserted into the gap.

15 Claims, 4 Drawing Sheets

ELECTRIC MOTORIZED TOOTHBRUSH WITH ROTATING SPINDLES

BACKGROUND OF THE INVENTION

Field of the Invention

The invention relates to an electric, motorized toothbrush having at least three rotating spindles that allow the user to simultaneously brush the top of the teeth, lip-side of the teeth, and tongue-side of the teeth.

Discussion of Related Art

Dental health professionals advise patients, regardless of age, to regularly care for teeth and gums by brushing, flossing, and using mouthwash. The goal of the care is to reduce plaque, germs, and particulates which, if not removed, may cause various health problems such as bad breath, tooth decay, gum disease, and other problems associated with plaque buildup such as gingivitis, cavities, nerve sensitivity, etc.

The toothbrush is a staple of this health care practice. Yet, the toothbrush is also one of the reasons for the failures associated with this health care regimen. For example, and in contrast to brushing with a toothbrush, flossing between teeth introduces friction between adjacent teeth directly moving and removing any particulates between the teeth. Also, mouthwash successfully reaches all surfaces within the mouth.

However, the toothbrush, which is clearly the most used and relied upon oral hygiene device, is considerably less efficient. Often, brushing does not remove all of the plaque or particulates in a person's mouth. Brushing is frequently unevenly applied to the teeth resulting in some teeth having been well brushed while others less so, leaving a hygienically significant amount of germs in the mouth. It is not uncommon for one's mouth to feel gritty and unclean shortly after brushing.

Brushing teeth, even if well done and complete, causes other problems. For example, the act of brushing with a manual toothbrush involves moving the brush along the surface of the teeth in parallel to the tooth plate. For the front teeth, this involves moving the toothbrush side to side. For the back teeth, this involves moving the toothbrush repeatedly into the mouth and then out of the mouth. In this standard application of use, the toothbrush rubs back-and-forth along the gum line, both in front of the teeth and behind the teeth. The problem with this motion is that, with aggressive brushing, forceful brushing, or simply long and/or frequent brushing, the gum, along the gum line, becomes sore from the abrasion with the toothbrush bristles. Although not necessarily painful, the gum often recedes from repeated aggression.

Receding gums lead to exposed lower parts of the teeth, more areas for germs to enter the gaps, breed, and penetrate deep into the gums. Obviously, this results in further cleanliness challenges. Receding gums can lead to loosened teeth, exposed and sensitive nerves, and associated cosmetic changes.

Often, people find that their mouths do not feel clean after brushing their teeth. Then, people may brush longer or more often, which exacerbates the problems noted above without the advantage of removing all of the plaque buildup and germs or evenly brushing. People may use mouthwash to make their teeth and mouth feel cleaner. However, when they rub their tongues along their teeth, people often feel unclean or unsmooth tooth surfaces, despite the brushing, flossing and mouthwash. Again, resolving the unclean feeling, by longer, aggressive brushing leads to even greater stress to the gums.

The horizontal movement of the toothbrush is also inefficient for reaching between teeth. Some toothbrushes on the market attempt to resolve this by having some bristles longer than others, so that the longer bristles may reach between teeth as the toothbrush passes. However, the side-to-side movement of the toothbrush reduces the effectiveness of reaching between teeth. To resolve this, people need to brush up and down so that bristles are scraping the gap between teeth instead of sliding the bristles past the gap. Yet, people find it difficult to brush up and down, especially in the back of the mouth. Hence, the manual toothbrush is considerably inefficient and ineffective at brushing between the teeth.

Electric toothbrushes provide a head of bristles that rotate automatically. When users put the head of bristles on the teeth, the rotation of the bristles rubs the teeth in a circular motion, thus scraping off surface particulates via the rotation. Like the manual toothbrush, the electric toothbrush theoretically reduces the degree to which one needs to move the brush back and forth along the teeth to achieve the same degree of friction. However, like the manual toothbrush, the electric toothbrush must still be moving along the teeth and is, therefore, used in the same manner as the manual toothbrush. Further, like the manual toothbrushes, the bristles stress the gum line, yet do so more aggressively. For the lower teeth, the rotating head along the front or back surface of the teeth have a downward orientation so that some bristles are moving downward. When the downward moving bristles hit the gum line of the lower teeth, the bristles push the gum line down, encouraging and accelerating the receding of the lower gums. Likewise, for the upper teeth, the rotating head along the front or back surface of the teeth have an upward orientation so that some of the bristles are moving upward. When the upward moving bristles hit the gum line of the upper teeth, the bristles push the gum line up, encouraging and accelerating the receding of the upper gums. Like the manual brushing, the electric toothbrush is not optimized to remove plaque and particulates between teeth since the movement of the toothbrush is across the gap between teeth.

In the prior art, such as US Pat. No. 20120174938 A1, electric toothbrushes typically have a single spindle of bristles directly attached to the spinning armature from the motor. There is no need for the toothbrush to have gearing as the direction of rotation is irrelevant. Further, there are no secondary spindles as the concept of multiple gearing and/or spindles with counter-rotation are not utilized. In fact, the prior art toothbrushes typically utilize a spinning spindle at the end of a motor, not different than attaching a spindle to an electric drill.

There is a need for a completely new toothbrush design explicitly created to address these and other issues.

SUMMARY OF THE INVENTION

One aspect of the invention relates to an electric toothbrush utilizing purpose-designed gears for specific spindle rotations, wherein the purpose-designed positioning of, preferably, three spindles allows the user to simultaneously brush the top of the teeth, lip-side of the teeth, and tongue-side of the teeth. The gearing is designed and positioned for rotation, counter-rotation and/or a combination thereof as two or more gears drive two or more spindles to enable the attached brushes to simultaneously clean or brush the top, outside and inside of the teeth. Brushing all three sides of the teeth simultaneously not only is efficient but far more effective in cleaning the entire tooth, gum, gap between the teeth, etc. than doing so in a non-simultaneous manner.

BRIEF DESCRIPTION OF THE DRAWING

For a better understanding of the present invention, reference is made to the following description and accompanying drawings, while the scope of the invention is set forth in the appended claims.

DESCRIPTION OF THE PREFERRED EMBODIMENT

Figure 1:
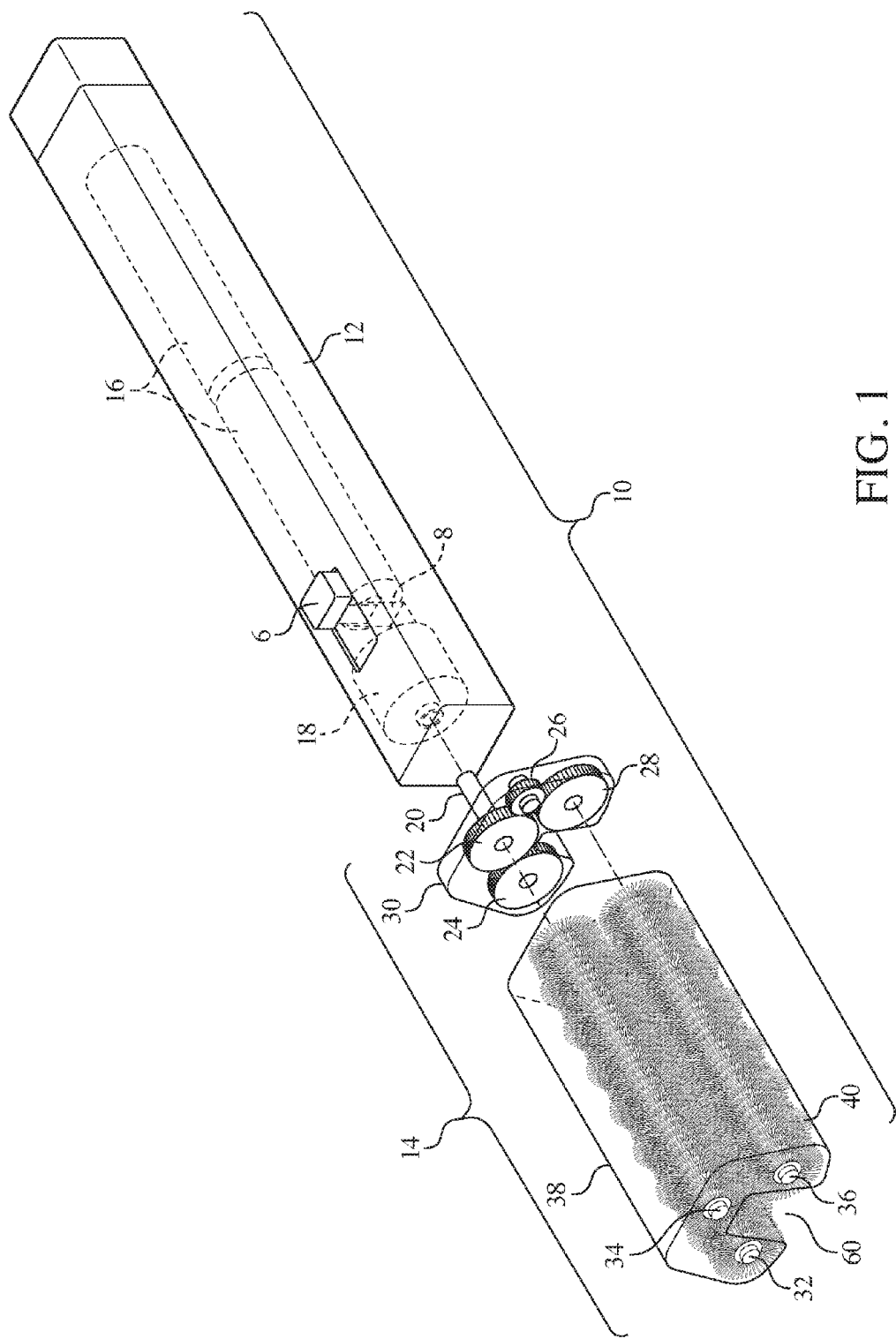
FIG. 1 is an isometric, exploded view of the electric, motorized toothbrush in accordance with the invention, but with the housing shown as if transparent to reveal components inside, namely, three spindles with brushes, a gear drive transmission, a motor, batteries, on/off switch, and connectors.
Figure 2:
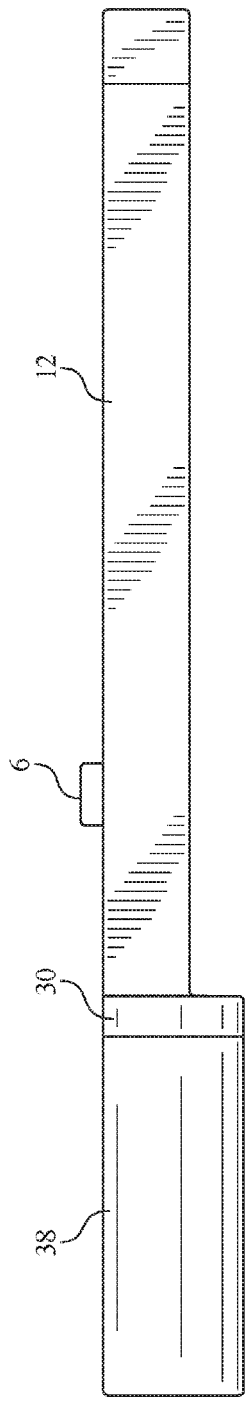
FIG. 2 is a side view of the electric, motorized toothbrush of FIG. 1 but with the housing shown opaque in accordance with the invention.

FIG. 1 shows one embodiment of the electric, motorized toothbrush 10 of this invention that has two segments: a handle 12 and a head 14. Inside the handle 12 of the toothbrush is a conventional power source such as a battery 16, which is electrically connected via connectors 8 in a conventional manner, such direct contact or wiring to a conventional on/off switch 6 and a conventional motor 18. Although FIG. 1 depicts two conventional AA type batteries as the power source 16, other conventional power sources, such as a 'plug in' circuit, a power cord which is wired to the motor 18, solar or other power cells, etc, could be utilized to drive the motor 18 instead of batteries and are encompassed by this disclosure. Also, as one of skill in the art should understand, the device utilizes conventional battery contacts and/or battery power circuitry (not shown) for retrieval of energy from the batteries for supplying power to the motor 18 and for the on/off switch 6 to activate the power source 16.

As the motor 18 spins, an armature from the motor rotates a motor drive shaft 20 that extends into the head 14 with a drive gear 22 attached to the motor drive shaft 20 within a gear drive transmission housing 30. Within the gear drive transmission housing 30 is also a set of three gears 24, 26, 28, which are respectively attached to three spindles 32, 34, 36 within a brush housing 38. Each of the spindles 32, 34, 36 have their own bristles 40 on them or, preferably, on a cylinder 42 (see FIG. 4) associated with each spindle. The drive gear 22 engages two of the three gears 24, 26 to drive them and one smaller gear 26 of the two driven gears engages the remaining third gear 28 to drive the same.

Figure 3:
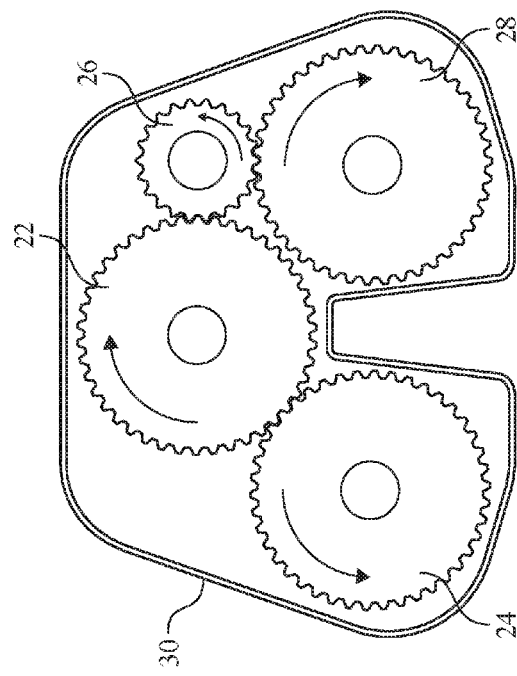
FIG. 3 is an end view of the gear drive transmission in accordance with the invention.

The alignment of the three gears 24, 26, 28 as shown in the gear drive transmission housing 30 depicted in FIG. 3 allows for counter-rotation, although the alignment could be for clockwise rotation and/or counter clockwise rotation instead of counter-rotation. It is the counter-rotation or rotation of the gears which then drive the spinning of the spindles as shown in FIG. 3. Collectively, the gears 22, 24, 26 and 28 shown in FIG. 3 may be considered a gear drive transmission.

Figure 4:
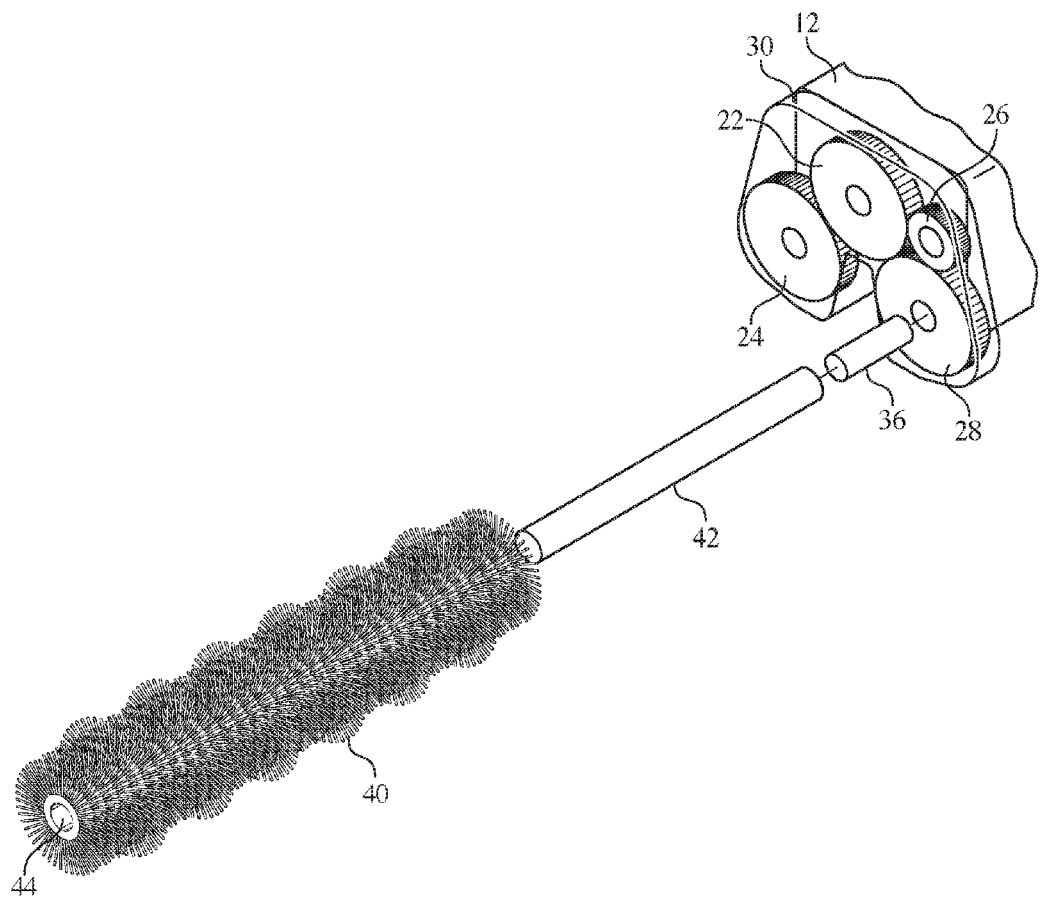
FIG. 4 is an isometric, exploded view of one of the brushes, one of the spindles, one of the cylinders that fit over the spindle and the gear drive transmission all in accordance with the invention.

FIG. 4 shows the manner that, in a preferred embodiment, one end of the spindle 36 can be inserted into, or otherwise connected to, gear 28 and the other end of spindle 36 can be inserted into a cylindrical cavity 44 of a cylinder 42 about which are arranged the bristles 40 in a conventional manner so as to form a rotatable bristle unit. The arrangement of the bristles 40 allow the bristles to be removed and replaced, such as by sliding the bristles assembled in a row in and out of a slot. In a like manner, one end of spindle 32 is inserted into, or connected to, gear 24 and the other end of spindle 32 into another cylindrical cavity 44 about which are arranged other bristles 40 so as to form a further rotatable bristle unit. In a like manner another rotatable bristle unit is formed with the remaining spindle 34 which is inserted into, or connected with, gear 22 on one end and into another cylindrical cavity 44 on the other end, about which are bristles 40. Once the three spindles 32, 34, 36 extend through the cylindrical cavity 44 of the three cylinders 42 from which radially extend the bristles 40, the distal ends may be retained in their relative position in a conventional manner yet permitting spindle rotation. It should be understood that the cylinders 42 should have a cavity 44 that fits tightly around each of the spindles 32, 34 and 36 so that the cylinders 42 rotate when the spindles 32,34, 36 rotate. Preferably the cylinders 42 are comprised of a material flexible enough so that the cylindrical cavity 44 fits flexibly but tightly over the spindles 32, 34, 36. Other conventional means to have the cylinder 42 cover each spindle 32, 34, 36 are covered by this invention as well. Likewise, the brushes 40 can be attached directly to each spindle 32, 34, 36, in which embodiment, there would be no need for cylinders 42 and associated cavity 44 depicted in FIG. 4. In such embodiment, the spindles 32, 34, 36, would replace the cylinders 42 in the above descriptions. In any event, whether the bristles 40 are attached to the cylinders 42 or the spindles 32, 34, 36, it is preferable to have the bristles 40 conventionally assembled in a manner that can be easily removed and replaced when the bristles are worn. Such replaceable bristle units may include a sleeve with bristles 40 attached thereto and wherein the sleeve slides in and out of a slot on the cylinders 42 or the spindles 32, 34, 36 in an embodiment without cylinders.

In the embodiment depicted in FIG. 1, the spindles 32, 34, 36 are positioned two on opposite sides of the head toward the bottom and one centrally at the top within the brush housing 38. The gears 22, 24, and 28 are positioned such that the two lower spindles rotate upward toward the top of the spindle in the manner indicated by rotation direction arrows in FIG. 3. The bottom of the brush housing 38 is open and the spindles 32, 34, 36 with bristles 40 are exposed. When the user puts the head over the teeth, the teeth are positioned or "sandwiched" between the two lower spindles 32, 36.

When cleaning teeth in the lower jaw, the two lower spindles 32, 36 are spinning in a manner that rotates the bristles 40 upward so the bristles spin away from the lower gum line, not toward the lower gum line as would be the case for conventional rotational electric toothbrushes. When cleaning teeth in the upper jaw, the two upper spindles 32, 36 are spinning in a manner that rotates the bristles 40 downward so the bristles 40 spin away from the upper gum line, not toward the upper gum line.

Figure 5:
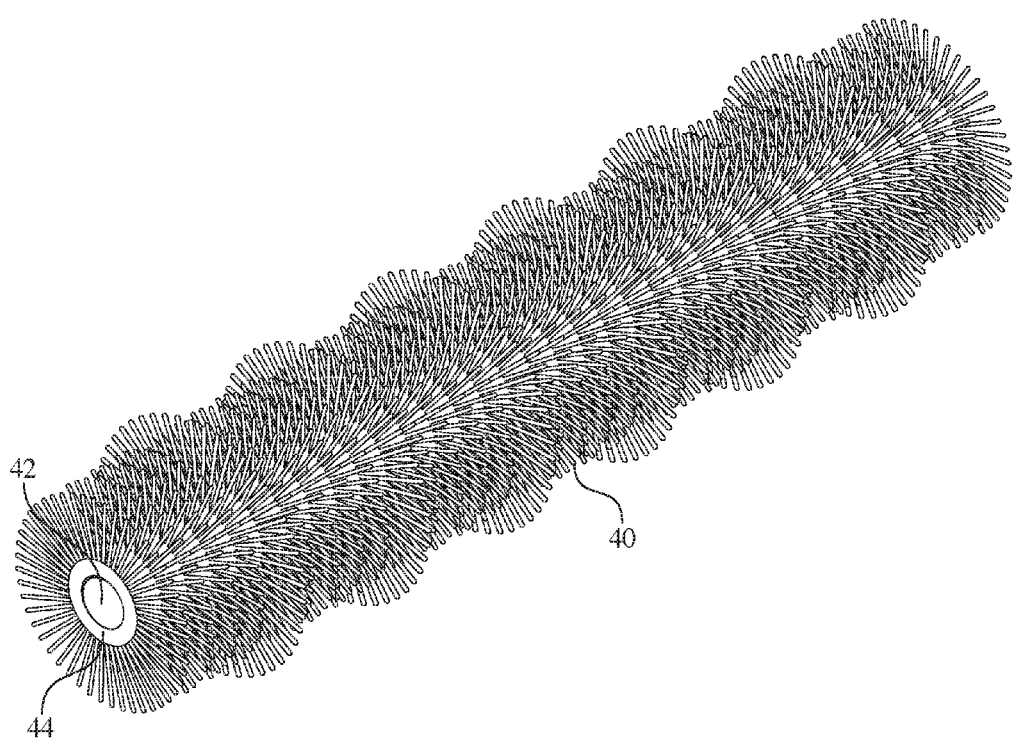
FIG. 5 is an isometric view of a brush in accordance with the invention.

As can be seen in FIG. 5, having some bristles 40 on the spindles 32, 34, 36 designed to be longer than others results in the vertical rotation of these longer bristles reaching between teeth that both manual and standard electric tooth brushes do not do. By having the spindles be wider than one tooth (which is not generally the case with standard electric tooth brushes) means the continuous rotation of the side spindles 32, 36 is more effective at providing friction against the tooth surface.

The top spindle 34 shown in FIG. 1 can rotate in either direction and takes care of providing the necessary friction of the top surface of the lower teeth. In another embodiment, the top spindle 34 can be geared in a manner than it moves forward and backward automatically rather than spin. If geared for reciprocating motion, it can be replaced with a bristle layout similar to conventional toothbrushes where all bristles face the same direction and are affixed to a common plate.

By turning the tooth brush over and using for the upper teeth, all benefits now become symmetrical. In this preferred embodiment, to optimize the brushing experience, the user repeats the brushing process for the top teeth as what was administered for the bottom teeth. The symmetric process achieves the same efficiencies, optimization, and effectiveness on the top as well as the bottom teeth.

As can be appreciated, one aspect of the invention pertains to an electric, motorized toothbrush that includes a handle 12 supporting a head 14, a motor driven gear drive transmission 22, 24, 26, 28 within at least one of the handle and the head, two bristle units 32,36 within the head 14, the two bristle units (with spindles 32,36) being driven into motion by the motor driven gear drive transmission to rotate in opposite directions relative to each other, and a third bristle unit (with spindle 34) that is adjacent to the gap 60 and closer to each of the two bristle units (with spindles 32, 36) than the two bristle units are to each other and being driven into motion by the motor driven gear drive transmission. The entire bristle units rotate in unison with their associated spindles in accord with any conventional manner of rotating spindles fitted within hollow cylinders 42 such as described above wherein each spindle fits tightly within the cylinder or with releasable gripping fasteners or any other conventional manner.

The two bristle units associated with spindles 32, 36 each have respective cylinders 42 with bristles 40 that extend in radially outward directions from the respective cylinders. These two bristle units are spaced apart from each other by the gap 60. The two bristle units (having spindles 32, 36) have a side facing the third bristle unit (having spindle 34). The head 14 includes the housing 38 that contains the two bristle units (having spindles 32, 36) and the third bristle unit (having spindle 34) yet leaves the gap 60 accessible from outside the housing. The two bristle units (having spindles 32, 36) carry out their rotation in the opposite directions by entering the gap 60 before reaching the side facing the third bristle unit (having spindle 34). Again, the bristle units can be easily replaced when worn; for example, a sleeve may be provided upon which the bristles are attached and the sleeve slides into a slot on the cylinders 42 or the spindles 32, 34, 36, depending on the embodiment.

While the foregoing description and drawings represent the preferred embodiments of the present invention, it will be understood that various changes and modifications may be made without departing from the scope of the present invention.

What is claimed is:

1. An electric, motorized toothbrush, comprising:
a handle supporting a head;
a motor driven gear drive transmission within at least one of the handle and the head;
two bristle units within the head, the two bristle units being driven into motion by the motor driven gear drive transmission to rotate in opposite direction relative to each other, the two bristle units each having respective spindles with bristles that extend in radially outward directions from the respective spindles, the two bristle units being spaced apart from each other by a gap; and
a third bristle unit that is adjacent to the gap and closer to each of the two bristle units than the two bristle units are to each other and being driven into motion by the motor driven gear drive transmission, the two bristle units each having a side facing the third bristle unit, the head including a housing that contains the two bristle units and the third bristle unit yet leaves the gap accessible from outside the housing;
wherein the two bristle units carry out their rotation in the opposite direction by entering the gap before reaching the side facing the third bristle unit.

2. The electric, motorized toothbrush of claim 1, wherein each of the respective spindles have repeating patterns of the bristles across a substantial length of the respective cylinders, some of the bristles having bristle lengths that are longer than the bristle lengths of the remaining bristles.

3. The electric, motorized toothbrush of claim 1, further comprising:
a power source within the handle that powers the motor.

4. The electric, motorized toothbrush of claim 1, wherein the two bristle units each include a respective cylinder with brushes into which is inserted an associated one of the respective spindles without brushes, the motor driven gear drive transmission being arranged to rotate the respective spindles that in turn rotate the respective cylinders and thereby the bristles.

5. The electric, motorized toothbrush of claim 1, wherein the gear drive transmission is within the head, further comprising a motor of the motor driven gear drive transmission that is within the handle.

6. The electric, motorized toothbrush of claim 1, wherein the motor driven gear drive transmission drives the third bristle unit to rotate.

7. The electric, motorized toothbrush of claim 1, wherein the motor driven gear drive transmission drives the third bristle unit in a reciprocating manner.

8. An electric, motorized toothbrush, comprising:
a head;
a motor driven gear drive transmission within the head;
two bristle units within the head, the two bristle units being driven into motion by the motor driven gear drive transmission to rotate in opposite direction relative to each other, the two bristle units each having respective spindles with bristles that extend in radially outward directions from the respective spindles, the two bristle units being spaced apart from each other by a gap; and
a third bristle unit that is adjacent the gap and closer to each of the two bristle units than the two bristle units are to each other and being driven into motion by the motor driven gear drive transmission, the two bristle units each having a side facing the third bristle unit, the head having a housing that contains the two bristle units and the third bristle unit yet leaves the gap accessible from outside the housing.
wherein the two bristle units carry out their rotation in the opposite direction by entering the gap before reaching the side facing the third bristle unit.

9. The electric, motorized toothbrush of claim 8, wherein each of the respective spindles have repeating patterns of the bristles across a substantial entire length of the respective cylinders, some of the bristles having bristle lengths that are longer than bristle lengths for the remaining bristles.

10. The electric, motorized toothbrush of claim 8, wherein the two bristle units each include a respective cylinder with bristles into which is inserted an associated one of the respective spindles without bristles, the motor driven gear drive transmission being arranged to rotate the respective spindles that in turn rotate the respective cylinders and thereby the bristles.

11. The electric, motorized toothbrush of claim 8, wherein the motor driven gear drive transmission drives the third bristle unit to rotate.

12. The electric, motorized toothbrush of claim 8, wherein the motor driven gear drive transmission drives the third bristle unit in a reciprocating manner.

13. A electric, motorized toothbrush head, comprising:
two bristle units each having respective spindles with bristles that extend in radially outward directions from the respective spindles, the two bristle units being spaced apart from each other by a gap;
a third bristle unit that is adjacent the gap yet closer to each of the two bristle units than the two bristle units are to each other; and
a housing that contains the two bristle units and the third bristle unit yet leaves the gap accessible from outside the housing.

14. The electric, motorized toothbrush of claim 13, wherein each of the respective spindles have repeating patterns of the bristles across a substantial entire length of the respective spindle, some of the bristles having bristle lengths that are longer than bristle lengths for the remaining bristles.

15. The electric, motorized toothbrush of claim 13, wherein the two bristle units each include a respective cylinder with bristles into which is inserted an associated one of the respective spindles without bristles, the motor driven gear drive transmission being arranged to rotate the respective spindles that in turn rotate the respective cylinders and thereby the bristles.

* * * * *